Figure 1:
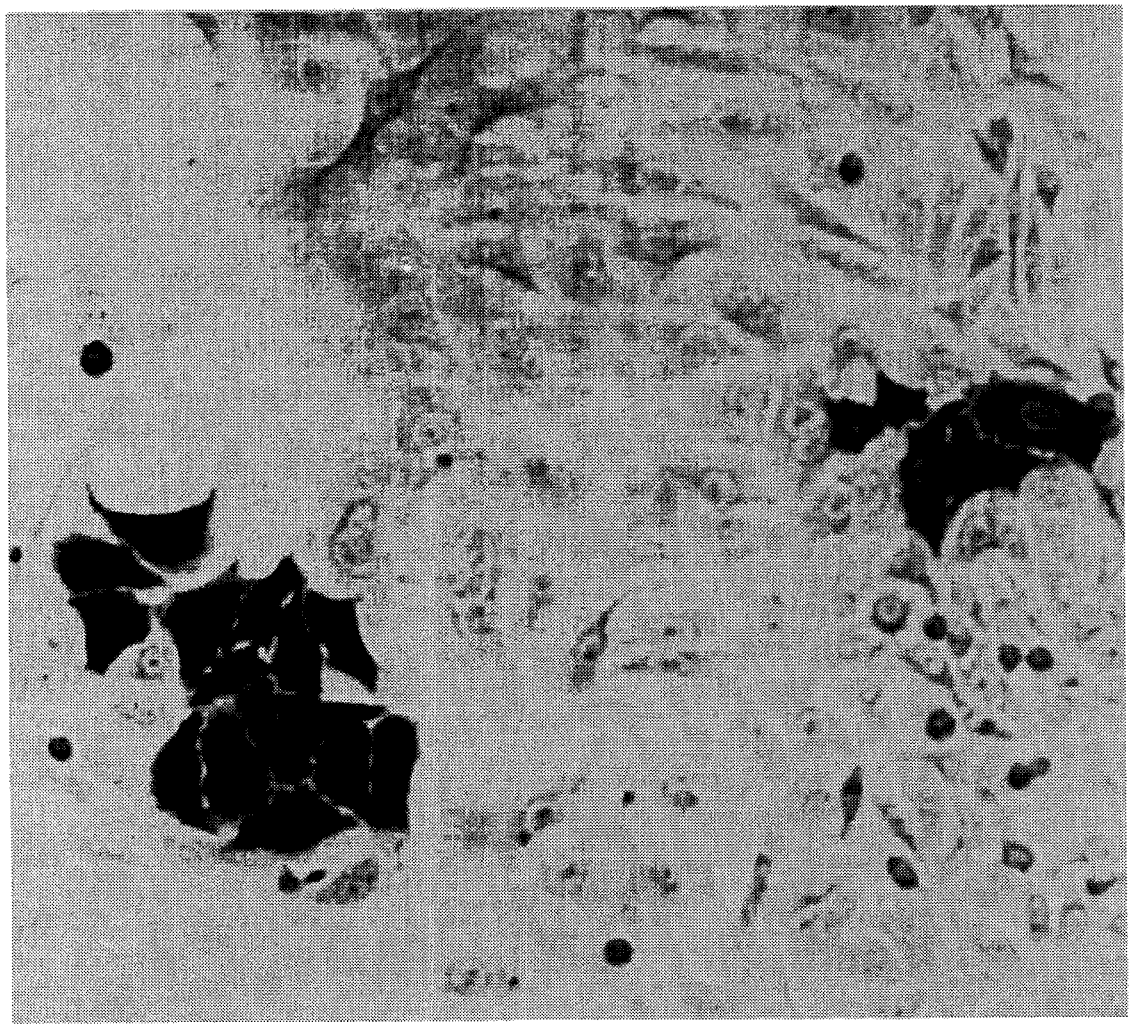

United States Patent [19]

Erfle et al.

[11] Patent Number: 5,582,967
[45] Date of Patent: Dec. 10, 1996

[54] HUMAN CELL LINE LC5 AND ITS USE

[75] Inventors: Volker Erfle, Munich; Werner Mellert, Lohhof, both of Germany

[73] Assignee: GSF Gesellschaft fur Strahlen-und Umweltforschung, Germany

[21] Appl. No.: 635,112

[22] PCT Filed: May 14, 1990

[86] PCT No.: PCT/EP90/00774
 § 371 Date: Nov. 13, 1991
 § 102(e) Date: Nov. 13, 1991

[87] PCT Pub. No.: WO90/14419
 PCT Pub. Date: Nov. 29, 1990

[30] Foreign Application Priority Data

May 18, 1989 [DE] Germany ............... 39 16 251.6

[51] Int. Cl.⁶ ........................ C12N 5/08; C12Q 1/70
[52] U.S. Cl. ............... 435/5; 435/240.1; 435/240.2
[58] Field of Search .............. 435/240.1, 240.2, 435/5

[56] References Cited

PUBLICATIONS

American Type Culture Collection Catalogue Of Cell Lines And Hybridomas. Fifth Edition, 1985. p. 5, ATCC CCL5, L–132.

M. J. Tocci et al (1984) Antimicrobial Agents And Chemotherapy vol. 25, No. 2:247–252.

*Primary Examiner*—John L. LeGuyader
*Attorney, Agent, or Firm*—Andrus, Sceales, Starke & Sawall

[57] ABSTRACT

The instant invention is drawn to human cell line LC5, ATCC CCL-5 and CNCM I-842, which are useful in a method of screening for retrovirus inhibitors.

6 Claims, 5 Drawing Sheets
(1 of 5 Drawing(s) in Color)

HUMAN CELL LINE LC5 AND ITS USE

This invention relates to the human cell line LC5, as well as to the use of same in the investigation of replication inhibition in retroviruses. In particular, this invention is concerned with the investigation of inhibitors and neutralizing antibodies for immunodeficiency viruses of human beings (HIV) and primates (SIV) through use of the human cell line LC5.

The in-vitro investigation of inhibitors for retroviruses has increased in importance in recent years, particularly in the area of AIDS research. It is the goal of this research to develop a therapy for HIV-infected persons. The investigations of neutralizing antibodies are especially interesting with respect to prognosis criteria for investigating the course of HIV infections and for the production of vaccines. In both areas of inquiry—both therapy as well as vaccination—a simple as possible technique for quantifying of the number of infectious viral units is imperative.

Up to now for the in-vitro investigation, cell lines susceptible to retroviruses were utilized, the cells of which grow in a medium. Such a liquid medium with the cell line which is infected with retro-viruses, for example HIV-1-strains, cannot immediately be drawn off, i.e. pipetted off, as the cells float in the medium and consequently could be drawn off along with the liquid medium. Hence, the medium must be allowed to stand some time until the infected cells have settled, so that the liquid medium produced in the meantime can be removed. But, even so, it is always possible that individual cells will again be agitated through the drawing off and are removed together with the liquid medium. Hence, the evaluation of how many cells have become infected by the retrovirus leads to inaccurate test results. Beyond that, a technique of this type is associated with an increased expenditure of work and time.

The large number of sera and substances coming into consideration that may be suitable as inhibitors, makes a rapid and reliable screening procedure necessary. This should be achieved, by way of example, in such a manner, that it could be automated. The use of cell lines in media permits no automation of the procedure, because of the above noted disadvantages.

The object of the invention is to disclose a cell line, that is susceptible to retroviruses and which permits a rapid and reliable investigation of sera and substances with regard to their suitability as inhibitors for retroviruses. In particular, an economical and time saving automation of such an investigation should be possible.

The object of the invention is achieved through the cell line LC5, which is susceptible to retroviruses, in particular to immunodeficiency viruses of human beings (HIV) and primates (SIV) and which can be infected with these viruses. The human cell line LC5 according to the invention is thus particularly suited for the investigation of inhibitors for retroviruses of this type. According to the invention, the use of this new cell line LC5 for the investigation of neutralizing sera and inhibitors for retroviruses is, thus, proposed. The invention further comprises the features of the dependent claims.

The cell line LC5 originates from the lung tissue of a human embryo (E.V. Dantes and V.S. Bolin Fed. Proc. 19, 386, 1960). The original human cell line is deposited under the designation L 132 in the American Type Culture Collection (ATCC, Nr. CCL-5). The cell line L 132 was repeatedly cultured, treated with antibiotics against mycoplasm and subcloned, by which means the cell line LC5 was obtained.

The cell line LC5 according to the invention was deposited on Mar. 9, 1989 in the National Collection of Cultures of Micro-organisms (CNCM), Paris, under Deposit Number I-842.

The human cell line LC5 according to the invention grows by adhering to plastic or glass surfaces, and thus the investigation of inhibitors for retroviruses can be automated in a problem free manner. Owing to the fact that the cell line grows by adhering to plastic and glass surfaces, there is no longer the danger that, with the drawing off, i.e. pipetting off, of the liquid medium, cells floating in the medium could be drawn off. As a result, full automation of the drawing off step is, in particular, possible.

The cells of the cell line LC5 grow as monolayer cultures in RPMI 1640 (Gibco) as the culture medium, that is mixed with 10% fetal calf serum at 37° C. and 5% $CO_2$. The morphology of the cells is epithelial. The cells exhibit typical features of mesenchyme cells such as lamina, fibrinectin, and vimentin, and additionally small amounts of cytokeratin.

The file of this patent contains at least one drawing executed in color. Copies of this patent with color drawings will be provided by the Patent and Trademark Office upon request and payment of the necessary fee.

Figure 2:
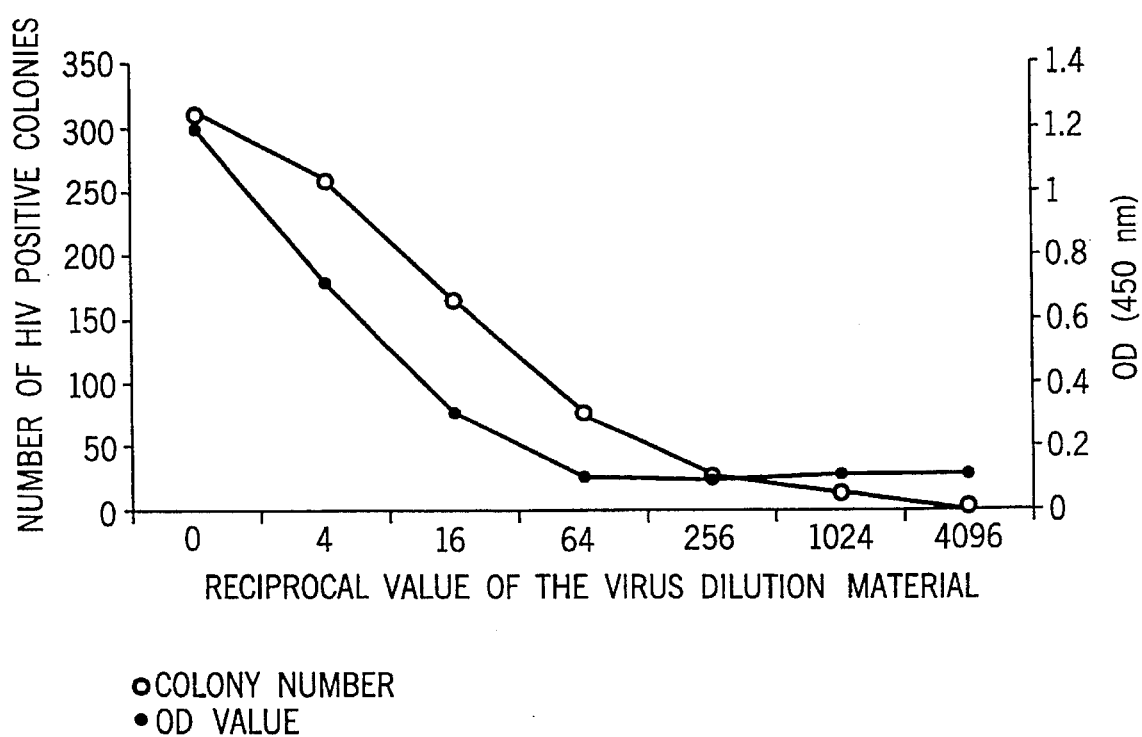
Figure 3:
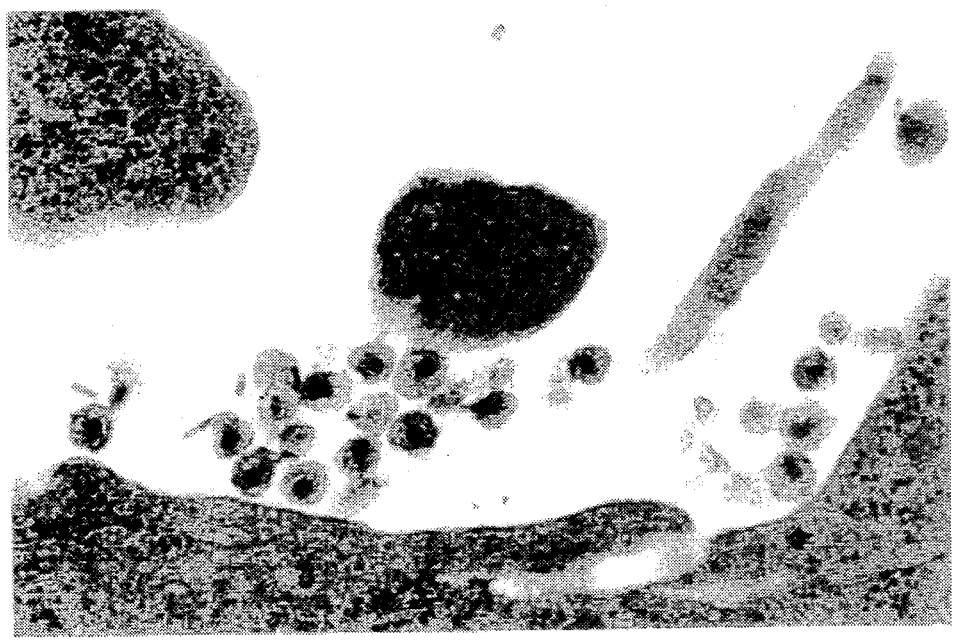
Figure 4:
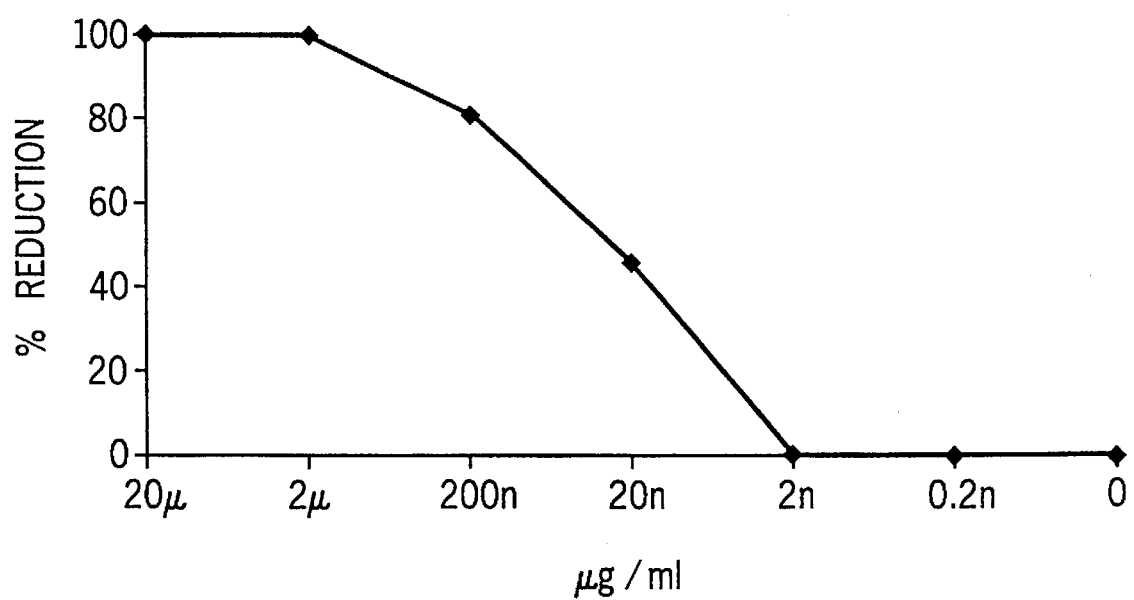
Figure 5:
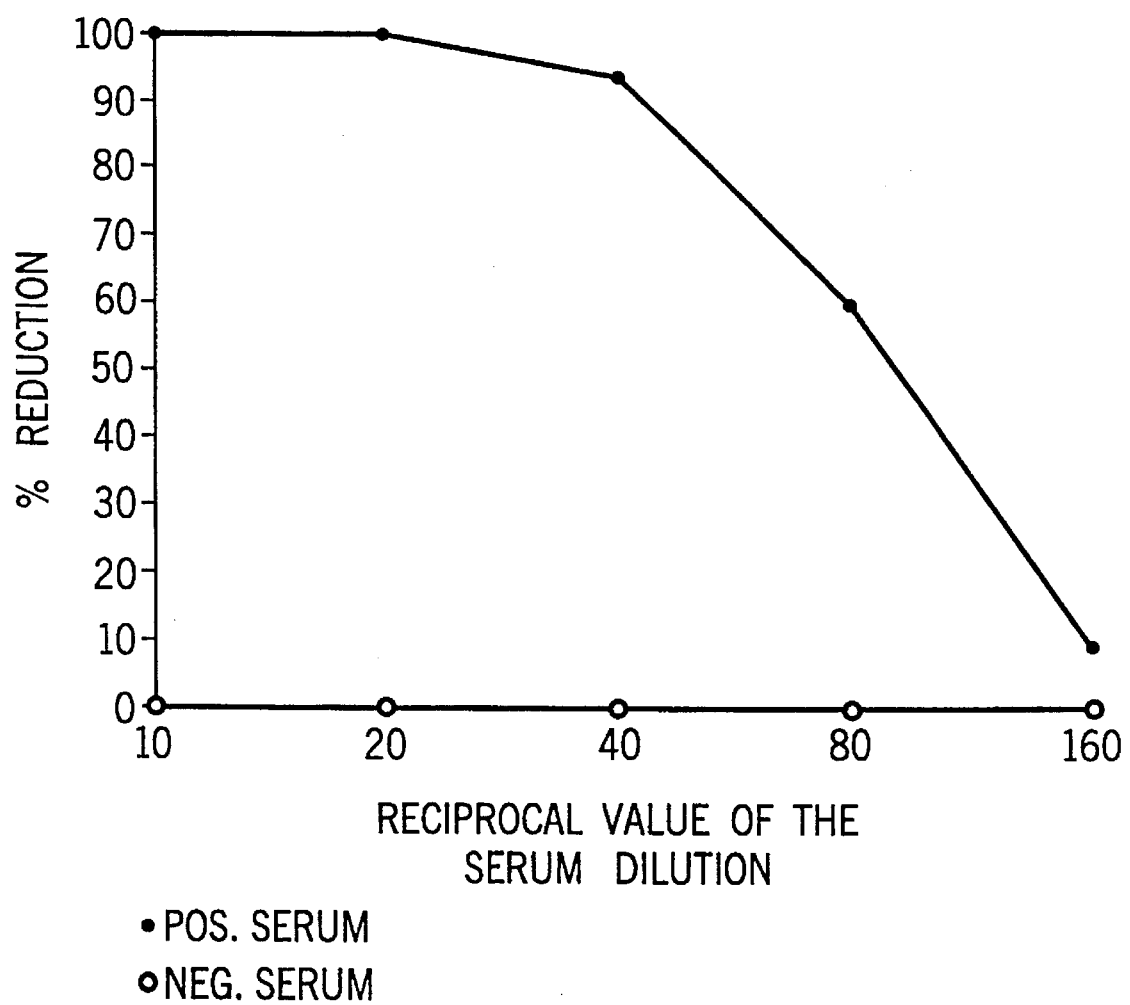

The invention is further explained below with reference to the drawings. The drawings show:

FIG. 1, a microscopic illustration of the LC5 cells after infection with HIV-1 and staining of the HIV-1 protein cells (colony);

FIG. 2, a correlation of the HIV-titers with the number of HIV-protein-positive colonies, respectively the color change in the supernatant;

FIG. 3, an electron microscopic view of the release of HIV-particles in the cell line LC5-HIV;

FIG. 4, the reduction of HIV positive LC5-colonies after treatment with dideoxycytidin (ddC); and FIG. 5, the reduction of HIV positive LC5-colonies through neutralization of HIV by means of a human serum, In the use of the human cell line LC5 for the in-vitro investigation of inhibitors, for example, for HIV, the human cell line LC5 was initially infected with different HIV-1 strains (HTLV IIIb, RF, Rutz) and with HIV-2. This led to the formation of 4–8 cell colonies after 3–4 days, that produced HIV-protein structures. The evidence of the HIV-protein structure production resulted from a serological test, through use of antibodies against these proteins (antibodies 1) and with a substrate directed against the corresponding immunoglobin, that contains antibodies coupled to peroxidase or phosphatase (antibodies 2). In this connection, 3-aminoethylcarbazol, which is insoluble in water, was used as the specific substrate. This process is known as the so-called indirect immunoperoxidase staining; compare in this respect Mellert et al. A1F01, 105–107, 1986. The number of stained colonies was determined under an optical microscope. FIG. 1 shows the cells of the human cell line LC5 infected with HIV-1, that have been stained with this staining process.

As is apparent from FIG. 2, the number of the HIV-protein producing colonies formed is directly proportional to the number of the infectious HIV-particles. For the determination of this direct proportionality, different virus concentrations were used for the infection of the human cell line LC5. FIG. 2 shows the number of HIV-positive colonies related to the reciprocal value of the virus dilution material used. With the use of a soluble substrate, for example, orthophenylendiamin (OD), a color change in the solution over the cells can be induced employing the stained cells or colonies. The intensity of the color change is directly proportional to the number of infectious HIV-particles with which the human cell line LC5 is infected. This is likewise apparent from FIG. 2.

The human cell line according to the invention was infected with HIV-1 and cloned after the infection through single cell dilution. The HIV positive cells were then allowed to grow to a cell line. This cell line is designated LC5-HIV and was likewise deposited with the CNCM in Paris on Mar. 9, 1989 under the deposit number I-843. The cell line LC5-HIV produces infectious particles in the surrounding medium in the range of about 105 infectious particles per milliliter in medium. In FIG. 3, an electron microscopic view of the release of HIV-particles in the cell line LC5-HIV is shown, enlarged 80,000 X.

A. INVESTIGATION OF INHIBITORS

The process according to the invention for the investigation of inhibitors for retroviruses through use of the human cell line LC5 and the cell line LC5-HIV was implemented, as follows, using HIV as the example.

The HIV infected LC5-HIV cells were treated for a period of approximately one week, then the investigation of infectious units in the culture supernatant followed through a new infection of non-infected LC5 cells with a following immunohistochemical determination of the number of HIV-positive colonies. HIV-infected human fetal lung cells LC5-HIV were used as virus producing cells and human fetal lung cells LC5 were used as non-infected cells. Both cell lines were cultured with RPMI 1640 (Gibco) and 10% fetal calf serum (FCS) at 37° C. and 5% $CO_2$.

As positive verification of an anti-HIV-effective therapeutic, dideoxycytidin (ddC) was used. This substance was used in different concentrations with a corresponding dilution progression in the range of 20 μg/ml to 0.2 ng/ml.

The treatment of the virus producing cells was implemented as follows. In 24 well test plates (Nunc) were placed $3 \times 10^3$ LC5-HIV cells in 1 ml of culture medium (RPMI 1640/10% FCS) and, within an hour, mixed with the different concentrations of the therapeutic dideoxycytidin (day 0). For each test concentration, four cultures were prepared. Thereafter, the cells were incubated for a period of a week at 37° C. and 5% $CO_2$, in the course of which, on days 3 and 5, the therapeutic was replenishingly added to the culture medium. On day 7, the plates were centifuged for a period of 10 minutes at 3,000 rpm, and 200 μl of supernatant per well of the test plates were pipetted off.

For the quantification of the infectious units in the supernatant, $2 \times 10^3$ LC5-cells in 100 μl of medium were, respectively, placed in 96-microtiter test plates and cultured for a period of three hours at 37° C. and 5% $CO_2$. The medium was drawn off, and 100 μl culture supernatant of the treated LC5-HIV cells, which was removed from the 24 well test plates, were added per well, such that for each well of the 24 well test plates, respectively, two cultures were added in the 96-microtiter test plates. The supernatant was left on the cells for an hour, then drawn off and replaced with 200 μl of fresh culture medium. The test plates were cultured for a period of three days at 37° C. and 5% $CO_2$. The determination of the number of HIV-positive colonies resulted through indirect immunoperoxidase staining. To this end, the cells were fixed with methanol/acetone (proportions 1:1, −20° C.) for a period of five minutes and dried in the air. The evidence of the HIV-protein structures was obtained by means of a HIV-antibody positive human reference serum [diluted 1:150 in PBS (phosphate buffered saline solution)] as well as the visualization of the antigen-antibody complex by means of rabbit-anti-human-IgG coupled in (horse radish) peroxidase through use of 3-aminoethylcarbazol/$H_2O_2$ as a substrate. The number of stained colonies was determined by means of an optical microscope.

It is apparent that the control substance dideoxycytidin (ddC) was not toxic at 20 μg/ml for the LC5-HIV cells. The number of HIV-positive LC5-colonies, that were formed through infection with the pre-treated culture supernatant, is to be taken from Table 1. The values given there represent an average of eight test data. In the following table, the standard deviation (SD), that is established, respectively, out of the eight test data for concentration, is, in each case, given.

TABLE 1

Number of HIV-positive colonies after infection of LC5-cells with supernatant from ddC-treated LC5-HIV cells

|  | 20 μg | 2 μg | 200 ng | 20 ng | 2 ng | 0.2 ng | 0 ng/ml |
|---|---|---|---|---|---|---|---|
| ddC:MW | 0 | 0 | 3.9* | 11.0 | 21.9 | 18.8 | 130.4 |
| SD |  |  | 1.9 | 3.0 | 4.6 | 6.6 | 21.1 |

MW = average value
SD = standard deviation
* = number of HIV-pos. LC5-colonies

The conversion of the colony number in percent reduction in comparison to an untreated control results in a reduction of the infectious units, as shown in FIG. 4. It is apparent from FIG. 4, that the treatment of LC5-HIV cells with dideoxycytidin up to a concentration of 2 μg/ml has, as a consequence, a 100 percentage reduction in the infectious units in the culture supernatant.

On the basis of these results, it can thereby be derived that the anti-HIV-effectiveness of different substances can be assessed through the manipulation of HIV-infected human fetal lung cells LC5-HIV and through the evaluation of the infectious units in the culture supernatant with LC5 cells as target cells. This system contemplates all possible points of application of a therapeutic (virus attachment, virus release, inactivation of free virus particles) and is thereby suitable as a screening system. Through use of monolayer cells, all process steps are fully automatable by means of an XYZ robot.

B. TESTING NEUTRALIZING ANTIBODIES

The process according to the invention for the testing of neutralizing antibodies through use of the human cell line LC5 as well as LC5-HIV was implemented, as follows, using HIV-1 as an example.

As the cell free HIV suspension, cell culture supernatant of LC5-HIV that had been extracted a week after passage of the cells, was used. The supernatant was centrifuged for 10 minutes at 1000 g and filtered by means of an ultrafilter (pore size 45 μm). To 50 μl of this supernatant, 50 μl of the test serum in different concentrations were added and incubated for one hour at room temperature. The quantification of the infectious units remaining after this incubation was carried out through innoculation of the LC5 cells with the serum-virus mixture according to the method described under point A.

It became apparent that in the presence of neutralizing antibodies, the number of HIV-positive LC5-colonies correlates with the serum dilution (Table 2). The values given in Table 2 represent, respectively, an average of four test data. In addition, the standard deviation (SD), that has been calculated from the four test data, is set out.

TABLE 2

| | Number of HIV-positive LC5 colonies in the presence of neutralizing antibodies | | | | |
|---|---|---|---|---|---|
| reciprocal serum dilution | 10 | 20 | 40 | 80 | 160 |
| pos. serum | 0 | 0 | 15(±6) | 93(±14) | 201(±29) |
| neg. serum | 187(±16) | 224(±32) | 218(±28) | 230(±23) | 219(±34) |

The translation of the colony number in percent reduction in comparison to an untreated control results in a reduction of the infectious units, as is shown in FIG. 5. It is apparent from FIG. 5, that the neutralizing serums provide, as a consequence, a reduction in the colony number of up to 100%. On the basis of these results, it can thereby be derived that through infection of LC5-cells, the neutralizing properties of serums (reduction of infectiousness of HIV) can be assessed.

We claim:

1. A method of screening for inhibitors of retroviruses comprising the step of treating a culture of a human cell line infected with an immunodeficiency virus of humans (HIV) or primates (SIV) with the inhibitor to be screened wherein the human cell line used is LC5-HIV having CNCM accession number I-843, followed by determination of the number of infectious units in the supernatant.

2. A method of screening for inhibitors or retroviruses comprising the step of treating a culture of a human cell line infected with an immunodeficiency virus of humans (HIV) or primates (SIV) with the inhibitor to be investigated, wherein the human cell line used is LC5 having CNCM accession number I-842, followed by determination of the number of infectious units in the supernatant.

3. A method of screening for inhibitors and neutralizing serums for immunodeficiency viruses of humans (HIV) or primates (SIV) using the human cell line LC5 with CNCM accession number I-842 characterized as treating LC5 cells infected with retrovirus though placing the infected cell line in a culture medium, in particular in RPMI 1640 containing 10% fetal calf serum, and adding an anti-retrovirus effective therapeutic;

incubating these cells for a determined period of time, in particular incubating the cells over a time period of a week at 37° C. and 5% $CO_2$;

quantifying the infectious units in the supernatant over the cells by means of the human cell line LC5; and determining the number of retrovirus-positive colonies, in particular by means of an indirect immunoperoxidase staining.

4. The method of claim 3 wherein said retrovirus is an immunodeficiency virus of humans.

5. A human cell line characterized in that it grows by adhering on plastic or glass surfaces and is susceptible to infection by immunodeficiency viruses of humans (HIV) or primates (SIV), obtained by subcloning of human cell line L-132 having ATCC accession number CCL-5 and said human cell line is LC5 with CNCM accession number I-842.

6. Human cell line LC5-HIV having CNCM accession number I-843.

* * * * *

UNITED STATES PATENT AND TRADEMARK OFFICE
CERTIFICATE OF CORRECTION

PATENT NO. : 5,582,967
DATED : December 10, 1996
INVENTOR(S) : Erfle et al

It is certified that error appears in the above-indentified patent and that said Letters Patent is hereby corrected as shown below:

CLAIM 2, Col. 5, Line 32, delete "investigated" and substitute therefor ---screened---

Signed and Sealed this

Ninth Day of September, 1997

Attest:

BRUCE LEHMAN

Attesting Officer

Commissioner of Patents and Trademarks